United States Patent [19]

Davis et al.

[11] 3,959,481

[45] May 25, 1976

[54] METHOD OF PROTECTING PLANTS FROM FUNGAL DISEASES USING FURAN-3-CARBOXAMIDE DERIVATIVES

[75] Inventors: Robert A. Davis, Cheshire; Bogislay von Schmeling, Hamden, both of Conn.; Ethel E. Felauer; Marshall Kulka, both of Guelph, Canada

[73] Assignee: Uniroyal, New York, N.Y.

[22] Filed: Feb. 13, 1969

[21] Appl. No.: 799,110

[52] U.S. Cl............................ 424/285; 260/347.3; 424/263; 424/270
[51] Int. Cl.² ........................................ A01N 9/28
[58] Field of Search................ 424/285, 263, 270

[56] References Cited
UNITED STATES PATENTS

| | | | |
|---|---|---|---|
| 3,152,136 | 10/1964 | Harris et al. | 424/285 |
| 3,352,663 | 11/1967 | Freund | 41/2.5 |
| 3,354,157 | 11/1967 | Leon et al. | 424/285 |

FOREIGN PATENTS OR APPLICATIONS

| | | | |
|---|---|---|---|
| 39-26571 | 11/1964 | Japan | 424/285 |

OTHER PUBLICATIONS

Hanson et al., −(Derivatives of 6-Aminopenicillanic Acid, Part IX, 2,4−D: and 2,46−Tri substituted−3−foryl penicillins, (1965), Chem. Dept., Beechanh Research Lab, Brockham Park, Betchworch, Surrey).

*Primary Examiner*—Frederick E. Waddell
*Attorney, Agent, or Firm*—Hubbell, Cohen, Stiefel & Gross

[57] ABSTRACT

A broad class of furan-3-carboxamide derivatives has been found to possess good fungicidal, insecticidal and nematocidal properties.

15 Claims, No Drawings

METHOD OF PROTECTING PLANTS FROM FUNGAL DISEASES USING FURAN-3-CARBOXAMIDE DERIVATIVES

This invention relates to antifungal and insecticidal chemicals of a broad class of furan-3-carboxamide derivatives of the following general formula:

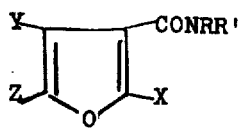

wherein R is hydrogen, methyl, or other alkyl, acyl, aroyl (e.g. benzoyl), sulfenyl (e.g. trichloromethyl sulfenyl); R' is hydrogen, alkyl, alkenyl, cycloalkyl, naphthyl, benzyl, pyridyl, thiazolyl, ethylene bis-, furylmethyl, phenyl or substituted phenyl. The phenyl substitution may consist of alkyl, alkoxy, nitro, halo, carboxy or phenyl such as in biphenyl. R and R' can be joined by forming heterocyclic groups such as by morpholido and other ring structures; X, Y and Z can be independently selected from hydrogen, $NH_2$-, alkyl, substituted alkyl (e.g. hydroxyalkyl, chloroalkyl, nitroalkyl), halo, alkenyl (e.g. allyl), Y and Z together are $\alpha$-$\omega$-alkylene (e.g. tetramethylene), phenyl, substituted phenyl (e.g. alkylphenyl, halophenyl, alkoxyphenyl).

Of the many furan-3-carboxamide derivatives that are within the invention, most are novel compounds which are fully described in the copending application of Felauer et al, Ser. No. 799,109, filed of even date herewith and assigned to the assignee of the instant application.

The broad class of furan-3-carboxamide derivatives can be prepared by reacting an $\alpha$-hydroxyketone or $\alpha$-hydroxyaldehyde (I) with an acetamide (II), in an inert solvent (such as benzene, toluene or xylene or mixtures thereof), with an active Friedel-Crafts reagent (such as $AlCl_3$, $AlBr_3$ or $SnCl_4$), to produce the carboxamide derivative (III), as follows:

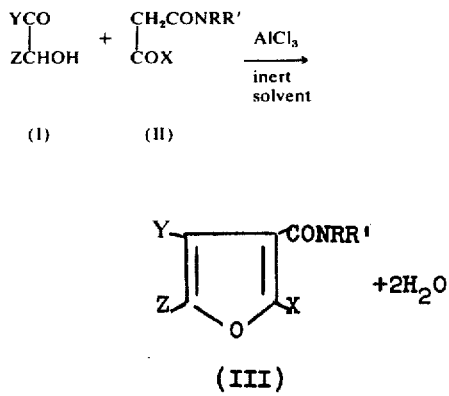

$AlCl_3$, $AlBr_3$ and $SnCl_4$ are preferred Friedel-Crafts reagents. ($ZnCl_2$ and $BF_3$, being weaker Friedel-Crafts reagents tend to produce pyrrole rather than furan structures.) It has been found convenient to use about 0.5 mole of the selected Friedel-Crafts reagent for each mole of $\alpha$-hydroxyketone or aldehyde or acetamide used and to use equimolar quantities of the latter reagents.

As indicated, the ring closure is accompanied by the expulsion of water and, accordingly, a strongly dehydrating Friedel-Crafts reagent is preferred. On the other hand, it is possible to remove the water of reaction by some other means (e.g. azeotropically) and to use just a catalytic amount of the Friedel-Crafts reagent (i.e. 0.01 to 0.5 mole per mole of $\alpha$-hydroxyketone or aldehyde or acetamide).

Since the Friedel-Crafts reagents reacts with hydroxy groups, it is preferable to employ anhydrous reactants and non-hydroxylic solvents such as, for example, in addition to those mentioned above, nitrobenzene, chlorobenzene, ethyl acetate and acetonitrile.

It is convenient to use equimolar amounts of the $\alpha$-hydroxyketone or $\alpha$-hydroxyaldehyde and acetamide reactants. The reaction is exothermic, although some heating to temperatures of about 50°C. or higher suffices. Preferably neither the initial temperature nor the temperature resulting from the heat of the exothermic reaction should exceed the boiling point of the reacting solution.

After completion of the reaction, the reacting solution is quenched with water and hydrochloric acid, the solvent layer is separated, and the product crystallized from solution.

The furan-3-carboxamide derivatives can also be made by using the foregoing process to obtain the basic furan-3-carboxamide structure (III), and then employing any well-known substitution reaction to provide a desired radical at any or all of the X, Y and Z positions, as well as at the R position.

One important aspect of the invention is the breadth of the class of furan-3-carboxamides which possesses the high degree of anti-fungal and other activity found. Another significant aspect is the wide variety of pathogens against which the compounds of the invention are notably effective.

Included within the invention are compounds possessing systemic activity against pathogens that are systemic in the plant or deeply embedded in plant tissue, and therefore not affected by ordinary protectant chemicals, e.g., *Ustilago nuda* (Jens.) Rostr. which causes Loose Smut of barley; and compounds effective against rust diseases, e.g., *Uromyces phaseoli* (Pers.) Wint. var. typica Arth. and Wheat Leaf Rust caused by *Puccinia rubigo-vera tritici* (D.C.) Wint., either by foliar application or by seed or soil treatment; and compounds which, either in treating soil or seed, can control seedling diseases caused by soil-borne organisms, such as *Rhizoctonia solani* Kuhn, which causes seedling decay in cotton; and compounds capable of affording protection from diseases, such as Early Blight of tomatoes caused by *Alternaria solani* (Ell. and G. Martin) Sor., by foliar application.

It should be pointed out that the furan-3-carboxamides should not be confused with certain known furan-2-carboxamide derivatives. Thus furan-2-carboxanilide and 3-methyl furan-2-carboxanilide each gave 0% control in the bean rust test of Example 1 below.

The following examples illustrate the invention:

Example 1 - Foliage spray treatment for control of established bean rust disease (*Uromyces phaseoli*).

Procedure

The ability to control plant diseases which are already established in the plants was evaluated by employing the following testing technique.

Two hundred milligrams chemical were dissolved in 20 ml of acetone and 60 mg of a surfactant such as Triton X-100.* This preparation was diluted with 80 ml distilled water giving a chemical suspension of 2000 ppm. Further serial dilutions were prepared from this as desired. The chemical suspensions were sprayed on duplicate pots, each containing two snapbean plants which had, 48 prior to this, been inoculated with bean rust *Uromyces phaseoli typica* Arth. At the time of the chemical spray the bean plants have just begun to expand their first trifoliate leaves. The test plants were then placed in a control chamber for 24 hours at 75°F and 100% relative humidity. After this time the plants were returned to the greenhouse. About 10 days later the plants were scored for disease control.

*Triton X-100 is octyl phenoxy polyethoxy ethanol (non ionic) Table 1. The systemic fungicidal effect of furan-3-carboxamides as measured by their ability to control established bean rust disease by foliage application.

Type I.

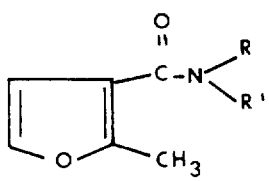

| R | R' | PPM | % Control |
|---|---|---|---|
| H | cyclohexyl | 2000 | 100 |
|  |  | 500 | 95 |
| " | phenyl | 250 | 100 |
|  |  | 125 | 90 |
| " | 2-tolyl | 500 | 100 |
| " | 3-tolyl | 500 | 100 |
|  |  | 125 | 90 |
| " | 4-tolyl | 2000 | 100 |
|  |  | 500 | 30 |
| " | 2-biphenylyl | 2000 | 100 |
|  |  | 500 | 80 |
| " | 3-methoxy phenyl | 500 | 100 |
|  |  | 250 | 99 |
| " | 4-methoxy phenyl | 2000 | 98 |
| " | 2-methyl-6-chloro phenyl | 2000 | 50 |
| " | 2-naphthyl | 2000 | 50 |
| CH₃ | phenyl | 2000 | 85 |

Type II.

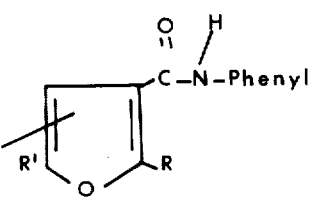

| | | | |
|---|---|---|---|
| 2,4-dimethyl-3-carboxanilido Furan | | 62 | 100 |
| | | 31 | 98 |
| 2,5-dimethyl-3-carboxanilido Furan | | 250 | 100 |
| 2-propyl-4,5-dimethyl carboxanilido Furan | | 2000 | 75 |

Type III

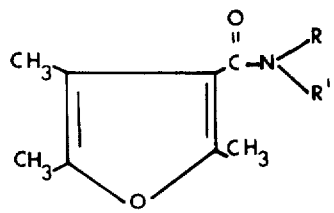

| R | R' | PPM | % Control |
|---|---|---|---|
| H | isopropyl | 500 | 80 |
| " | n-butyl | 500 | 99 |
| " | cyclohexyl | 62 | 95 |
| " | allyl | 500 | 75 |
| " | phenyl | 31 | 100 |
|  |  | 16 | 100 |
| " | 2-tolyl | 62 | 100 |
|  |  | 31 | 98 |
| " | 3-tolyl | 62 | 99 |
|  |  | 31 | 70 |
| " | 4-tolyl | 500 | 100 |
|  |  | 62 | 78 |
| " | 2,6-dimethyl phenyl | 2000 | 50 |
| " | 2,4,6-trimethyl phenyl | 2000 | 90 |
| " | 2-biphenylyl | 2000 | 50 |
| " | 2-methoxy phenyl | 2000 | 100 |
| " | 3-methoxy phenyl | 125 | 100 |
|  |  | 62 | 95 |
| " | 4-methoxy phenyl | 62 | 99 |
| " | α-naphthyl | 2000 | 60 |
| CH₃ | phenyl | 500 | 100 |

Example 2. Foliage spray treatment for preventing the establishment of bean rust disease (*Uromyces phaseoli*).

Procedure

A number of Pinto beans were sprayed with 100 and 50 ppm dosages of certain chemicals of the invention and the plants were kept in a greenhouse environment at 75°F. At intervals of 0, 1, 2, 3, and 4 days after chemical application a number of plants were removed from the greenhouse, inoculated with *Uromyces phaseoli* and kept in a moist chamber for 24 hours to initiate infection. The plants were then removed to the greenhouse. Symptoms appeared in about 5 days and chemical treatments were evaluated by the extent of disease development in the treated plants as compared to the non-treated controls.

Results

Table II.

Control of bean rust (*Uromyces phaseoli*), duration of protection by foliage spray of furan-3-carboxamides.

Protection Test
% Control When Treated X Days Before Inoculation With Rust

| Chemical | PPM | 0 | 1 | 2 | 3 | 4 |
|---|---|---|---|---|---|---|
| 3-carbox- | 200 | 100 | 100 | 100 | 100 | 100 |
| anilido-2,4,5 | 100 | 100 | 100 | 100 | 100 | 100 |
| trimethyl | 50 | 100 | 100 | 100 | 100 | 99 |
| furan | | | | | | |
| 2,4,5-tri- | 200 | 100 | 100 | 95 | 85 | 80 |
| methyl-3-(2- | 100 | 100 | 100 | 40 | 60 | 40 |
| methyl carbox- | 50 | 100 | 98 | 20 | 50 | 0 |
| anilido) furan | | | | | | |

Control - Severe infection

Plants sprayed with 50 ppm 3-carboxanilido-2,4,5-trimethylfuran were effectively protected against infection by the bean rust fungus.

Example 3. Eradication of bean rust infection by foliar application of furan-3-carboxamides.

A number of Pinto beans were inoculated with the bean rust fungus, *Uromyces phaseoli*, and the disease was allowed to become established. Plants were then sprayed with certain chemicals of the invention at 2, 3, 4, 5, and 6 days after inoculation with the fungus to determine the eradicant action of the chemicals. After spraying with the chemicals, the plants were returned to the greenhouse and disease development was evaluated in the usual manner after about 10 days. Chemicals were evaluated on the basis of their ability to eliminate the fungus infection from the plant or to stop its development.

Results

Table III.

| Chemical | PPM | % Control At Time Intervals - Days after Inoculation | | | | |
|---|---|---|---|---|---|---|
| | | 2 | 3 | 4 | 5 | 6 |
| 3-carboxanilido-2,4,5- | | | | | | |
| trimethyl furan | 50 | — | 100 | 100 | 98 | 60 |
| " | 100 | 97 | 100 | 100 | 100 | 90 |
| " | 200 | 99 | 100 | 100 | 100 | 95 |
| 2,4,5-trimethyl 3-(2-methyl carboxanilido) | | | | | | |
| furan | 50 | — | 100 | 100 | 100 | 30 |
| " | 100 | 100 | 100 | 100 | 100 | 80 |
| " | 200 | 100 | 100 | 100 | 100 | 93 |
| Untreated | | (severe infection) | | | | |

As can be seen from the above data, the chemicals of the invention gave eradication of the rust disease up to 6 days after the inoculation.

Example 4. Soil treatment for control of seedling diseases.

Chemicals of this invention were evaluated as soil fungicides for their effectiveness in controlling soilborne plant seedling diseases such as post-emergence damping-off of cotton seedlings caused by *Rhizoctonia solani* Kühn.

Procedure

The test method used was as follows:

Sixty-six mg. of the chemical were thoroughly mixed in a glass jar with one pound of clean, dry sand. The mixing was accomplished by vigorously shaking the covered jar. This masterbatch was then thoroughly mixed with 6-¼ pounds of soil to give a 20 ppm (parts per million) concentration of chemical. The treated soil was then placed into five 4 inch diameter pots in which 5 cotton seeds per pot, (Variety Stoneville 213) were planted. Before covering the planted seed the pots were inoculated by placing a grain of oats, infested with *Rhizoctonia solani* Kühn from a two week old culture, in the center of each pot. The seed and the inoculum were then covered with a layer of soil about ½ inch thick. Five replications were used giving a total of 25 seeds for each chemical treatment. An untreated control, replicated five times and planted and inoculated with the fungus in the same manner, was included in the test along with a similar control set which was not inoculated with the fungus.

After planting, the pots were then transferred to the greenhouse, watered and kept under warm, moist conditions by subirrigating and maintaining a 72°F. to 78°F. soil temperature. Results were taken two to three weeks later by counting the number of emerged and surviving cotton seedlings. The percent stand of cotton seedlings was calculated using the following formula:

$$\text{Percent stand} = \frac{\text{number of seedlings surviving}}{\text{number of seedlings emerged}} \times 100$$

The percent control was determined by using the following formula:

$$\% \text{ Control} = \frac{A-B}{C-B} \times 100$$

where A = % stand in treated inoculated soil.
B = % stand in untreated inoculated soil.
C = % stand in untreated non-inoculated soil.

Results

The following table gives the percent emergence and percent stand of cotton seedlings for treatment (40 ppm) with the chemicals listed, as compared to the untreated inoculated and untreated uninoculated soil controls. (40 ppm is equivalent to an application rate of 1.2 pound/acre treated area 2 inches wide and 2 inches deep; parallel rows in one direction; a distance of 40 inches apart).

Table IV.

The fungicidal effect of Furan-3-carboxamides as measured by their ability to control soilborne plant seedling disease.

Type I

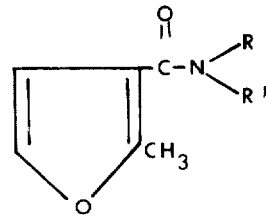

| R=H | R' | PPM | % Emerg. | % Stand | % Control |
|---|---|---|---|---|---|
| " | cyclohexyl | 40 | 88 | 48 | 39 |
|  |  | 10 | 92 | 56 | 54 |
| " | ethylene bis- | 40 | 84 | 52 | 40 |
| " | phenyl | 40 | 96 | 92 | 100 |
|  |  | 10 | 84 | 76 | 80 |
| " | 3-tolyl | 40 | 92 | 88 | 84 |
|  |  | 10 | 96 | 76 | 62 |
| " | 4-tolyl | 40 | 96 | 88 | 86 |
|  |  | 10 | 88 | 68 | 50 |
| " | 2,6-dimethyl phenyl | 40 | 92 | 60 | 53 |
|  |  | 10 | 88 | 44 | 27 |
| " | 2,4,6-tri-methyl phenyl | 40 | 72 | 60 | 62 |
|  |  | 10 | 92 | 52 | 46 |
| " | 2-methoxy phenyl | 40 | 88 | 72 | 57 |
|  |  | 10 | 88 | 56 | 29 |
| " | 3-methoxy phenyl | 40 | 96 | 76 | 92 |
|  |  | 10 | 92 | 64 | 69 |
| " | 4-methoxy phenyl | 40 | 92 | 88 | 86 |
|  |  | 10 | 92 | 76 | 64 |
| " | 4-nitro phenyl | 40 | 72 | 56 | 54 |
| " | 2-thiazolyl | 40 | 92 | 68 | 64 |
|  |  | 10 | 88 | 52 | 36 |

Type III

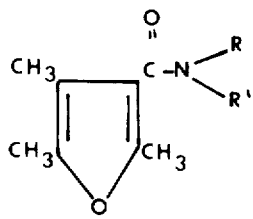

| R=H | R' | PPM | % Emerg. | % Stand | % Control |
|---|---|---|---|---|---|
| " | H | 40 | 92 | 72 | 54 |
|  |  | 10 | 88 | 60 | 31 |
| " | isopropyl | 40 | 88 | 76 | 62 |
| " | butyl | 40 | 92 | 72 | 54 |
|  |  | 10 | 96 | 64 | 38 |
| " | cyclohexyl | 40 | 100 | 96 | 100 |
|  |  | 10 | 92 | 84 | 83 |
| " | allyl | 40 | 96 | 80 | 69 |
|  |  | 10 | 92 | 68 | 46 |
| " | benzyl | 40 | 92 | 56 | 47 |
| " | phenyl | 40 | 88 | 84 | 70 |
|  |  | 10 | 88 | 80 | 60 |
| " | 2-tolyl | 40 | 96 | 92 | 93 |
|  |  | 10 | 88 | 76 | 64 |
| " | 3-tolyl | 40 | 100 | 92 | 93 |
|  |  | 10 | 96 | 76 | 64 |
| " | 4-tolyl | 40 | 92 | 76 | 64 |
| " | 2,6-dimethyl phenyl | 40 | 96 | 88 | 92 |
|  |  | 10 | 96 | 76 | 67 |
| " | 2,4,6-tri-methyl phenyl | 40 | 92 | 88 | 92 |
|  |  | 10 | 100 | 80 | 75 |
| " | 2-methoxy phenyl | 40 | 96 | 90 | 93 |
|  |  | 10 | 92 | 72 | 57 |
| " | 3-methoxy phenyl | 40 | 96 | 92 | 100 |
|  |  | 10 | 100 | 84 | 83 |
| " | 4-methoxy phenyl | 40 | 92 | 84 | 77 |
|  |  | 10 | 96 | 76 | 62 |
| " | 4-chloro phenyl | 40 | 88 | 64 | 57 |
| " | 2-chloro-6-methyl phenyl | 40 | 96 | 76 | 67 |
|  |  | 10 | 88 | 68 | 50 |
| " | α-naphthyl | 40 | 92 | 72 | 71 |
| " | 2-pyridyl | 40 | 96 | 80 | 85 |
|  |  | 10 | 88 | 60 | 46 |
| R=ethyl | ethyl | 40 | 88 | 64 | 54 |

Type II

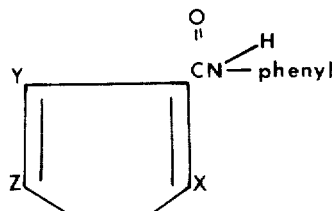

| X | Y | Z | PPM | % Emerg. | % Stand | % Control |
|---|---|---|---|---|---|---|
| methyl | methyl | H | 40 | 88 | 80 | 70 |
|  |  |  | 10 | 90 | 88 | 84 |
| methyl | H | methyl | 40 | 84 | 76 | 78 |
|  |  |  | 10 | 88 | 68 | 64 |
| propyl | methyl | methyl | 40 | 100 | 92 | 100 |
|  |  |  | 10 | 96 | 84 | 77 |
| methyl | phenyl | phenyl | 40 | 92 | 68 | 48 |
| phenyl | methyl | methyl | 40 | 80 | 64 | 48 |
|  |  |  | 10 | 84 | 60 | 36 |
| Untreated inoculated soil (control) | | | — | 88 | 56 | 0 |
| Untreated uninoculated soil (control) | | | — | 96 | 96 | — |

Table IV above shows the effectiveness of the chemicals of this invention as soil fungicides in preventing *Rhizoctonia* incited damping-off of cotton seedlings.

Example 5. FOLIAGE spray of furan-3-carboxamides for protecting tomato plants from infection by the early blight fungus, *Alternaria solani*.

This example evaluates the chemicals of the present invention as foliage fungicides by their ability to protect plants from subsequent infection by fungus diseases.

Procedure

One gram of the chemical to be tested was ground with three ml of acetone and 50 mg of a non-ionic surface-active agent (Triton X-100, a condensation product of an alkyl phenol and ethylene oxide). The acetone and surface-active agent are known to be inactive in the biological tests run. The mixture was diluted with water, giving suspensions containing 500 and 2000 ppm of the chemical. These suspensions were sprayed on duplicate 6 inch tomato plants (variety Clark's Early Special) using a gun-type sprayer. The plants were then placed in the greenhouse, together with untreated check plants. Twenty-four hours later the treated and untreated check plants were inoculated with a suspension of *Alternaria solani* spores by means of a 20 second spray from an atomizer sprayer (delivery rate 1 ml per second). The plants were then kept overnight in a controlled chamber at a temperature of 75°F. and 100% relative humidity. In the morning the plants were transferred to the greenhouse. Three days layer the disease was scored by comparing the number of disease lesions of the treated plants with the untreated control. The formula used to determine percent control is:

$$100 - \frac{(\text{Avg. no. lesions on treated plant})}{(\text{Avg. no. lesions on untreated plant})} \times 100 = \text{percent control}$$

Results

Table V

Control of tomato early blight disease by foliage application of furan-3-carboxamides.

Type I

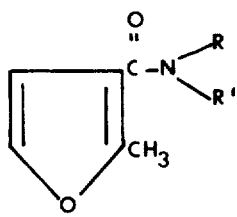

| R=H | R' | PPM | % Control |
|---|---|---|---|
| '' | phenyl | 500 | 83 |
| '' | 2-tolyl | 2000 | 87 |
|  |  | 500 | 65 |
| '' | 3-tolyl | 2000 | 75 |
|  |  | 500 | 50 |
| '' | 4-tolyl | 2000 | 75 |
|  |  | 500 | 88 |
| '' | 2,6-dimethylphenyl | 2000 | 71 |
|  |  | 500 | 67 |
| '' | 2-biphenylyl | 2000 | 100 |
|  |  | 500 | 99 |
| '' | 2-methoxy phenyl | 500 | 90 |
|  |  | 125 | 79 |
| '' | 3-methoxy phenyl | 500 | 75 |
| '' | 4-chloro phenyl | 2000 | 98 |
|  |  | 500 | 72 |
| '' | 2,4-dichloro phenyl | 2000 | 83 |
|  |  | 500 | 77 |
| '' | 2-methyl-6-chloro phenyl | 2000 | 74 |
|  |  | 500 | 77 |
| '' | 2-carboxy phenyl | 2000 | 75 |
|  |  | 500 | 50 |
| '' | α-naphthyl | 2000 | 81 |
|  |  | 500 | 67 |
| '' | 2-thiazolyl | 2000 | 99 |
|  |  | 500 | 93 |
| '' | H | 2000 | 50 |
| '' | n-butyl | 2000 | 75 |
| '' | cyclohexyl | 2000 | 75 |
|  |  | 500 | 50 |
| '' | decyl | 2000 | 50 |
| '' | allyl | 2000 | 50 |
| '' | furyl methyl | 2000 | 71 |

Type III

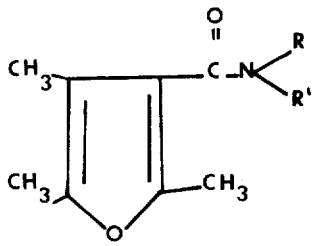

| | | | |
|---|---|---|---|
| '' | H | 2000 | 90 |
|  |  | 500 | 78 |
| '' | isopropyl | 2000 | 96 |
|  |  | 500 | 76 |
| '' | n-butyl | 2000 | 98 |
|  |  | 500 | 90 |
| '' | cyclohexyl | 2000 | 99 |
|  |  | 500 | 99 |
| '' | decyl | 2000 | 90 |
|  |  | 500 | 88 |
| '' | allyl | 2000 | 90 |
|  |  | 500 | 73 |
| '' | benzyl | 2000 | 96 |
|  |  | 500 | 79 |
| '' | furylmethyl | 2000 | 98 |
|  |  | 500 | 85 |
| '' | phenyl | 2000 | 80 |
|  |  | 500 | 70 |
| '' | 2-tolyl | 2000 | 85 |
|  |  | 500 | 78 |
| '' | 3-tolyl | 500 | 87 |
| '' | 4-tolyl | 2000 | 88 |
|  |  | 500 | 84 |
| '' | 2,6-dimethyl phenyl | 2000 | 50 |
| '' | 2,4,6-trimethyl phenyl | 2000 | 50 |
|  |  | 500 | 50 |
| '' | 2-biphenylyl | 2000 | 90 |
|  |  | 500 | 87 |
| '' | 2-methoxy phenyl | 2000 | 79 |
|  |  | 500 | 77 |
| '' | 3-methoxy phenyl | 2000 | 90 |
|  |  | 500 | 50 |
| '' | 4-methoxy phenyl | 2000 | 74 |
| '' | 4-chloro phenyl | 2000 | 76 |
|  |  | 500 | 67 |
| '' | 2-carboxy phenyl | 2000 | 78 |
|  |  | 500 | 50 |
| '' | α-naphthyl | 2000 | 77 |
|  |  | 500 | 70 |
| '' | β-naphthyl | 2000 | 87 |
|  |  | 500 | 77 |
| '' | 2-pyridyl | 2000 | 81 |
|  |  | 500 | 50 |

As demonstrated by the results shown in Table V, the chemicals of this invention are effective protective fungicides.

Example 6. Wheat leaf rust control by seed treatment with furan-3-carboxamides.

Certain chemicals of the invention were applied to wheat seeds by tumbling an appropriate quantity of chemical with 50 gram seed lots in small glass jars for 35 minutes. The seeds were planted in a standard soil mixture and were allowed to germinate under greenhouse conditions. After 5 days the leaves (3–4 inches tall) were inoculated with the leaf rust fungus, *Puccinia rubigo-vera tritici*, by spraying with spores suspended in a light mineral oil. Plants were kept in a moist chamber for 8 hours and transferred to the greenhouse having a temperature of 75°F. Symptoms appeared after 5 days and the chemical treatments were evaluated for effectiveness by the amount of reduction of the rust infection in treated plants as compared to the untreated controls.

Results

Table VI.

| Chemical | Wheat leaf rust control. OZ/CWT | % Control |
|---|---|---|
| 3-carboxanilido-2,4,5 trimethyl furan | 3 1½ | 99 95 |

Example 7. Wheat leaf rust control by foliar application of furan-3-carboxamides.

Procedure

Five day old Ceres wheat seedlings were inoculated with the fungus, *Puccinia rubigo-vera tritici*, by spraying with spores suspended in light mineral oil. Plants were kept in a moist chamber for 8 hours and transferred to the greenhouse having a temperature of 75°F.

One day after inoculation, a number of chemicals of the invention were applied to the wheat seedlings by dissolving the chemical in acetone, suspending it in water to which a wetting agent was added (Aerosol OT-B, American Cyanamid - dioctyl ester of sodium sulfo succinic acid) and spraying to runoff with a de Vilbiss sprayer delivering 1 ml/sec at 20 psi.

Rust disease symptoms appeared after 5 days and the chemical treatments were evaluated for effectiveness in disease control.

Results

Table VII.

Wheat leaf rust control by foliar application of furan-3-carboxamides.

| Chemical | PPM (Active) Foliar Application | % Control |
|---|---|---|
| 3-carboxanilido-2,4,5 trimethyl furan | 500 250 | 95 50 |
| 2,4-dimethyl-3-carboxanilido furan | 500 | 90 |
| 2,4,5-trimethyl-3-carboxanilido-N-benzoyl furan | 200 100 | 97 98 |

Example 8. Evaluation of Furan-3-carboxamide derivatives for control of a systemic disease, Barley Loose Smut (*Ustilago nuda*).

Procedure

Chemicals of the invention were evaluated for control of the Barley Loose Smut disease by seed treatment with the chemicals. Fifty gram seed lots of barly (variety Larker) approximately 20% infected with *Ustilago nuda* were treated with the experimental chemicals and a standard seed treatment chemical by tumbling the seed with the prescribed amount of dry-formulated chemical. Seeds from each chemical treatment were weighed in 10 gram lots of approximately 300 seeds each, and planted in replicated field plots of 25 feet each. Counts of the numbers of smutted grain heads were made approximately 10 weeks after planting.

Results

Table VIII

Control of Barley Loose Smut by seed treatment with furan-3-carboxamide derivatives.

Type I

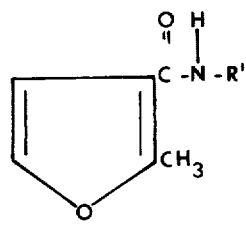

| | R' | oz/cwt | % Disease |
|---|---|---|---|
| | phenyl | 6 | 0.24 |
| | | 1½ | 1.70 |
| | 2-tolyl | 4 | 0.2 |
| | 3-tolyl | 4 | 0.0 |
| | | 1½ | 1.0 |
| Type II | Compound 2,4-dimethyl-3-carboxanilido furan | 4 1½ 1 | 0.0 0.04 1.8 |
| | 2,5-dimethyl-3-carboxanilido furan | 6 3 | 0 0 |

Type III

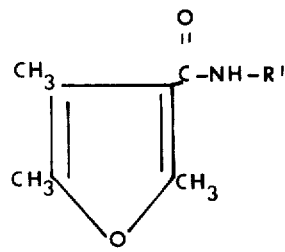

| R' | | |
|---|---|---|
| phenyl | 1 | 0 |
| | ½ | 0 |
| | ¼ | 0 |
| 2-tolyl | 4 | 0 |
| | 1½ | 0 |
| 3-tolyl | 4 | 0 |
| | 1½ | 0 |
| 3-methoxy phenyl | 6 | 0 |
| | 3 | 0 |
| 2-pyridyl | 4 | 0.3 |
| Control (untreated) | 1½ | 1.6 |
| | | 14.4 |

The chemicals of the invention have also been found to possess insecticidal and nematocidal activity. By insecticidal activity is meant activity with respect to insects, insect larvae and eggs.

Example 9. Insecticidal use of furan-3-carboxamides.

Procedure

Insecticidal activity of these chemicals was determined by adding 10 mg. of each chemical in 1 ml of acetone to 100 ml of water. Further dilutions were made from this solution using water as the diluent.

25 ml aliquots of each dosage, replicated once, were placed in test tubes and from 10 - 25 *Aedes aegypti* 4th instar larvae were added. The tubes were held at 70°F in darkness for 72 hours. At the end of this period the live and dead larvae were counted and percent control calculated. DDT at 0.1, 0.01, and 0.001 ppm was used as a standard. Appropriate formulation controls were also used.

Evaluation for ovicidal activity was accomplished by adding 0.1 g of each chemical in 1 ml of acetone to 50 ml of distilled water to which 1 drop of an emulsifier was added. This was sprayed on the lower surface of 2 week old bean plants each of which carried at least one egg mass of the Mexican Bean bettle (*Epilachna varivestes*) deposited 3–5 days prior to testing. Plants were sprayed to give a thorough coverage but not to saturation. At the end of one week the percentage of unhatched eggs was estimated.

The activity of furan-3-carboxamides against the corn leaf aphid (*Rhapalosiphum maidis* Fitch) was also investigated. A 2000 ppm solution was prepared by adding 0.5 g of chemical in 10 ml of acetone to 250 ml of water containing 2 drops of an emulsifier, Triton X-100.

Two days prior to spraying, the barley plants used for testing were thinned to 10 plants per cup and infested with aphids by placing clipped leaves from aphid-culture pots adjacent to the test plants. The plants were sprayed on a turntable to completely wet the leaves with the spray material. The percent control was estimated based on the reduction of population density on the treated plants as compared to untreated controls.

Results

Table IX.

Insecticidal use of furan-3-carboxamides.

| -R' | % Control Aedes aegypti (Larvae) 100ppm | % Control Aedes aegypti (Larvae) 10ppm | Mexican Bean Beetle Eggs % Control (Ovacide) 2000 ppm | % Control Corn Leaf Aphid (Contact) 2000 ppm | % Control Corn Leaf Aphid (Contact) 1000 ppm |
|---|---|---|---|---|---|
| cyclohexyl | 71 | — | 100 | 90 | 80 |
| decyl | 100 | — | 100 | — | — |
| benzyl | 80 | — | 100 | — | — |
| phenyl | 100 | 45 | 50 | — | — |
| 2-tolyl | 100 | 100 | — | — | — |
| 3-tolyl | 100 | 38 | — | — | — |
| 4-tolyl | 100 | — | 100 | — | — |
| 2-methoxy phenyl | 100 | — | — | — | — |
| 3-methoxy phenyl | 82 | — | — | 80 | — |
| 4-methoxy phenyl | 98 | — | — | — | — |
| 2-naphthyl | 85 | — | — | — | — |

| R' | -Xn | % Control Aedes aegypti (Larvae) 100ppm | % Control Aedes aegypti (Larvae) 10ppm | Mexican Bean Beetle Eggs % Control (Ovacide) 2000 ppm |
|---|---|---|---|---|
| phenyl | 2,4-dimethyl | 98 | — | |
| 2-methoxy phenyl | 2,4,5-trimethyl | 100 | 45 | |
| 4-chlorophenyl | 2,4,5-trimethyl | — | — | 100 |
| phenyl | 2-heptadecyl-4,5-dimethyl | 58 | — | 100 |
| | | 100 | — | 100 |

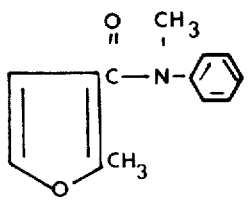

Example 10. Nematocidal activity of furan-3-carboxamides.

Procedure

A.

Contact nematocidal activity of the furan-3-carboxamides was determined by dissolving 300 mg of each compound in 10 ml of acetone and adding 3 drops of the solution to a watch glass containing 5 drops of a standardized nematode suspension (*Panagrellus redivivus*). Watch glasses were kept at room temperature in a moisture saturated environment to reduce evaporation of test liquids. Appropriate untreated and formulation controls were included in each test. 24 and 48 hours after treatment the watch glasses were examined microscopically and the percent kill was estimated.

Table X(A)

Nematocidal activity of furan-3-carboxamides

| R' | PPM | Panagrellus Nematode % Control |
|---|---|---|
| n-butyl | 1000 | 100 |
| cyclohexyl | 1000 | 90 |
| benzyl | 1000 | 100 |
| phenyl | 1000 | 100 |
| 2-tolyl | 1000 | 80 |
| 4-tolyl | 1000 | 95 |
| 2-methoxy phenyl | 1000 | 98 |
| 4-methoxy phenyl | 1000 | 90 |
| 2-methyl, N-methyl furan-3-carbox-anilido | 1000 | 97 |

B.

The efficiency of furan-3-carboxamides in controlling soil-borne root knot nematodes (*Meloidogyne sp.*) was examined by adding the chemical to the soil which is infested with a given proportion of nematode infested soil. Application rates of 60, 120 and 240 pounds per acre were used.

Dry treatments were accomplished by mixing the appropriate amount of chemical with ¼ pound of sand, adding this to ½ pound of soil and tumbling the mixture in a blender for 5 minutes.

Soil was placed in 12 ounce containers and kept in a greenhouse environment for 1 week after treatment. Cucumber seeds were then planted and roots of the plants were examined after 2 weeks and notes were made on the number of root knots in treated soil compared to the untreated soil.

Liquid treatments were done by mixing the appropriate amount of chemical in 2–4 ml of acetone, with 25 ml of distilled water containing one drop of Triton X-100. The liquid was then added gradually to ¾ pound of the soil preparation and mixed with a suitable garden tool. The soil was placed in 12 ounce cups and the test was carried out as described above.

Table X(B)

Percent control of cucumber root knot disease by furan-3-carboxamides.

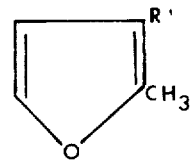

| R' | lbs. active/acre | % control |
|---|---|---|
| 2-methyl carboxanilido | 125 | 30 |
| 2-methoxy carboxanilido | 250 | 25 |
| 4-methoxy carboxanilido | 250 | 70 |
| N-methyl carboxanilido | 250 | 85 |
| N-methyl carboxanilido | 125 | 25 |
| N,N-diethyl carboxamido | 250 | 80 |
| N-isopropyl carboxamido | 250 | 80 |
| N-morpholino carbonyl | 250 | 80 |
| carbethoxy | 250 | 40 |
| 2-methyl-4,5-diphenyl 3-carboxanilido furan | 250 | 30 |

In light of all the data herein, it is evident that a truly broad class of chemicals has been found to possess broad fungicidal properties. Thus the chemicals of the invention have been shown to be effective against systemic as well as non-systemic pathogens, and it has further been demonstrated that these chemicals can be applied via soil, seed, seedling or foliar treatments. When introduced into the soil, the chemicals can simply be admixed therewith. When foliar application is contemplated, any obvious and well-known expedient by which spraying is accomplished is acceptable, e.g., the active chemical is incorporated into any standard carrier solution employing common diluent together with a wetting agent so that the surface of the foliage is adequately wetted by the solution.

It has also been shown that the furan chemicals of the invention are effective as insecticidal and nematocidal agents. Their use as such, as in the case of their fungicidal use, is made possible by any of the well-known expedients for applying the chemicals to locations where insect or nematode activity is known or expected.

Furthermore, it should be evident to those in the art that any number of the disclosed compounds can be admixed with each other, or other fungicides, insecticides or nematocides to yield effective and active compositions. All such variations are considered as within the scope of the appended claims.

Having thus described our invention, what we claim and desire to protect by Letters Patent is:

1. A method of protecting plants from fungal diseases comprising contacting the fungus with a fungicidally effective amount of a compound of the formula:

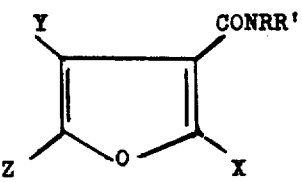

wherein R is selected from the group consisting of hydrogen, alkyl containing from 1 to 10 carbon atoms, benzoyl and trichloromethylsulfenyl; R' is selected from the group consisting of hydrogen, alkyl containing 1 to 10 carbon atoms, alkenyl containing 2 or 3 carbon atoms, cyclohexyl, naphthyl, benzyl, pyridyl, thiazolyl, ethylene bis-, N-furylmethyl, phenyl, biphenylyl, and substituted phenyl wherein the substituents are selected from the group consisting of methyl, methoxy, nitro, halo, and carboxy, and X, Y and Z are independently selected from the group consisting of hydrogen, alkyl containing 1 to 17 carbon atoms, allyl, phenyl, and substituted phenyl wherein the substituents are selected from the group consisting of halo and nitro, or Y and Z together are 1,4-butylene.

2. The method of claim 1 wherein the compound is 2-methylfuran-3-carboxanilide.

3. The method of claim 1 wherein the compound is 2,4-dimethylfuran-3-carboxanilide.

4. The method of claim 1 wherein the compound is 2,4,5-trimethylfuran-3-carboxanilide.

5. The method of claim 1 wherein said compound is applied to the plant by foliar application.

6. The method of claim 1 wherein the compound is N,2,4,5-tetramethylfuran-3-carboxanilide.

7. The method of claim 1 wherein the compound is 2,5-dimethylfuran-3-carboxanilide.

8. A method as claimed in claim 7, wherein said compound is applied to leaves of plants.

9. A method as claimed in claim 7, wherein said compound is applied in the soil.

10. A method for protecting plants from fungal diseases comprising contacting the plant seed with a fungicidally effective amount of a compound of the formula:

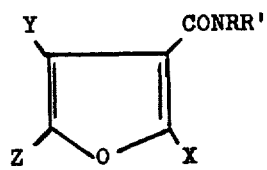

wherein R is selected from the group consisting of hydrogen, alkyl containing from 1 to 10 carbon atoms, benzoyl and trichloromethylsulfenyl; R' is selected from the group consisting of hydrogen, alkyl containing 1 to 10 carbon atoms, alkenyl containing 2 or 3 carbon atoms, cyclohexyl, naphthyl, benzyl, pyridyl, thiazolyl, ethylene bis-, N-furylmethyl, phenyl, biphenylyl, and substituted phenyl wherein the substituents are selected from the group consisting of methyl, methoxy, nitro, halo, and carboxy, and X, Y and Z are independently selected from the group consisting of hydrogen, alkyl containing 1 to 17 carbon atoms, allyl, phenyl, and substituted phenyl wherein the substituents are selected from the group consisting of halo and nitro or Y and Z together are 1,4-butylene.

11. A method for protecting plants from fungal diseases comprising admixing the soil to be used for plant growth with a fungicidaly effective amount of a compound of the formula:

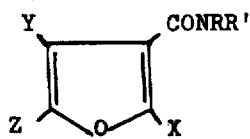

wherein R is selected from the group consisting of hydrogen, alkyl containing from 1 to 10 carbon atoms, benzoyl and trichloromethylsulfenyl; R' is selected from the group consisting of hydrogen, alkyl containing 1 to 10 carbon atoms, alkenyl containing 2 or 3 carbon atoms, cyclohexyl, naphthyl, benzyl, pyridyl, thiazolyl, ethylene bis-, N-furylmethyl, phenyl, biphenylyl, and substituted phenyl wherein the substituents are selected from the group consisting of methyl, methoxy, nitro, halo, and carboxy, and X, Y and Z are independently selected from the group consisting of hydrogen, alkyl containing 1 to 17 carbon atoms, allyl, phenyl, and substituted phenyl wherein the substituents are selected from the group consisting of halo and nitro, or Y and Z together are 1,4-butylene.

12. A method for protecting plants from fungal diseases comprising contacting the plant seed with 2,4,5-trimethylfuran-3-carboxanilide.

13. A method for protecting plants from fungal diseases comprising contacting the plant seed with 2,5-dimethylfuran-3-carboxanilide.

14. A method for protecting plants from fungal diseases comprising contacting the plant seed with 2,4-dimethylfuran-3-carboxanilide.

15. A method for protecting plants from fungal diseases comprising contacting the plant seed with 2-methylfuran-3-carboxanilide.

* * * * *